United States Patent
Fukumoto

(10) Patent No.: US 6,420,076 B1
(45) Date of Patent: Jul. 16, 2002

(54) METHOD AND APPARATUS OF INSPECTING FOREIGN SUBSTANCE ON SUBSTRATE SURFACE

(75) Inventor: Hirofumi Fukumoto, Toyama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 1262 days.

(21) Appl. No.: 08/523,075

(22) Filed: Aug. 31, 1995

(51) Int. Cl.[7] .................. G01N 21/88; G01N 23/225
(52) U.S. Cl. .................. 430/30; 430/330; 430/20; 356/237; 348/704; 348/706; 348/712; 348/725; 216/23; 216/24; 216/49; 216/60; 216/66; 134/1.2; 134/1.3
(58) Field of Search ............... 430/20, 30, 320, 430/323, 311, 317, 330, 331; 356/237; 134/1.2, 1.3, 3; 156/626.1, 643.1, 646.1, 650.1, 659.11, 704, 712; 216/23, 24, 42, 49, 60, 63, 64, 74; 348/706, 725

(56) References Cited

U.S. PATENT DOCUMENTS

| | | | |
|---|---|---|---|
| 4,468,120 A | * 8/1984 | Tanimoto et al. | 356/237 |
| 4,586,822 A | 5/1986 | Tanimoto | 359/394 |
| 4,824,769 A | * 4/1989 | Lewis et al. | 430/331 |
| 4,900,938 A | * 2/1990 | Suzuki et al. | 250/442.2 |
| 4,900,939 A | 2/1990 | Aoyama | 250/548 |
| 5,096,802 A | * 3/1992 | Hu | 430/328 |
| 5,252,881 A | * 10/1993 | Muller et al. | 310/309 |

FOREIGN PATENT DOCUMENTS

| | | | | |
|---|---|---|---|---|
| JP | 60-145616 | * | 8/1985 | 430/328 |
| JP | 1-73242 | * | 3/1989 | 356/237 |
| JP | 4-147641 | * | 5/1992 | |
| JP | 62-46239 | * | 2/1997 | 356/237 |

OTHER PUBLICATIONS

"Solid State Technology", Jul. 1990, pp. S1–S8.
Elliot, David J., "Integrated circuit fabrication technology" © 1982 pp 6–9, 166–171,210–213,233–243,282,283 and 302–305.*
"Rinsing Method for Locating Stain in a Semiconductor Wafer", by Yoshiichi Knoishi, *Surface Control of Washing Design*, Spring 1988 w/Translation.

* cited by examiner

Primary Examiner—Martin Angebranndt
(74) Attorney, Agent, or Firm—Merchant & Gould PC

(57) ABSTRACT

This invention comprises an inspection method conducted by rotary-coating a photoresist on the surface of a semiconductor substrate, irradiating ultraviolet rays using an exposure instrument such as a stepper, exposing the entire photoresist, removing the exposed photoresist using an alkali developing solution, and irradiating a laser beam onto the semiconductor substrate to detect foreign substances through the scattered light. Accordingly, gel foreign substances remain on the semiconductor substrate even after the steps of exposure and development, so that their presence can be detected surely. Furthermore, this invention provides a method and an apparatus of surely detecting gel foreign substances which are present in a photoresist film or between patterns by exposing the photoresist and performing etching and ashing, using gel foreign substances which remained through the development as a mask. A photoresist is rotary-coated on a wafer, and ultraviolet rays are irradiated on the photoresist using an exposure instrument such as a stepper, thereby exposing the entire wafer. Then, the photoresist is removed with an alkali developing solution, and the wafer which has the photoresist removed is etched, ashed, and washed. A laser beam is irradiated on the surface of the ashed wafer, and foreign substances are inspected from the reflecting scattered light.

16 Claims, 6 Drawing Sheets

FIG. 1 (a)
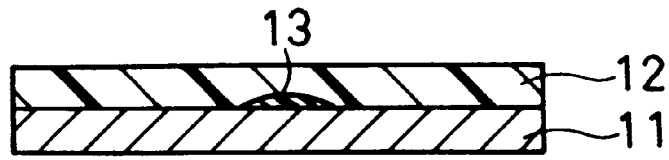
FIG. 1 (b)
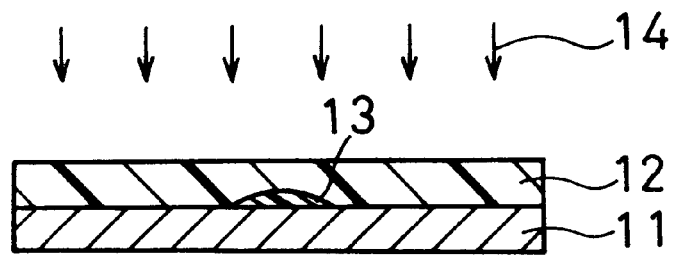
FIG. 1 (c)
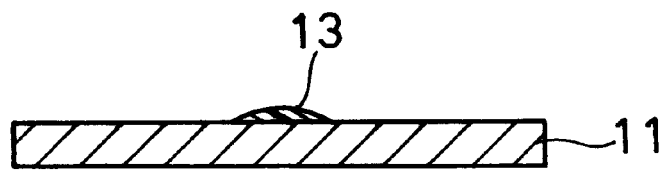
FIG. 1 (d)
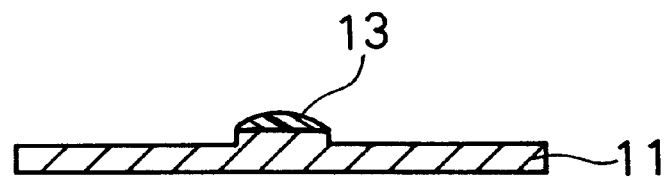
FIG. 1 (e)
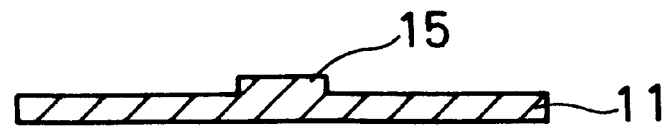
FIG. 1 (f)
INSPECTION OF FOREIGN SUBSTANCES FIG. 3(d) | INSPECTION OF FOREIGN SUBSTANCES

METHOD AND APPARATUS OF INSPECTING FOREIGN SUBSTANCE ON SUBSTRATE SURFACE

FIELD OF THE INVENTION

This invention relates to a method of inspecting foreign substances in the form of, for example, gel which are contained in a photoresist (including a photosensitive resin) applied onto substrates, such as a semiconductor substrate, a printed circuit substrate, a connector substrate for electric connection, a nesa glass for liquid crystal display element, and various sensors. This invention further relates to an apparatus of inspecting foreign substances applying the aforementioned method.

BACKGROUND OF THE INVENTION

Substrates, such as a semiconductor substrate, a printed circuit substrate, a connector substrate for electric connection, a nesa glass for liquid crystal display element, and various sensors, generally use a photoresist film to conduct exposure and development so that fine and accurate wiring patterns can be formed on the surface. However, since a photoresist film has a complicated molecular structure, when becoming insoluble through photoirradiation or conversely when becoming soluble to an alkali solution through photoirradiation, or when a photoresist film is affected by an abnormal charge or a partial heating during the manufacturing process of resin, gel substances may be occasionally created.

A silicon semiconductor substrate will be used as an example for this explanation. FIG. 5 is a schematic cross-sectional view showing a conventional apparatus used to inspect for foreign substances in a photoresist film. According to this conventional apparatus for inspecting for foreign substances in a photoresist film, a wafer 31 is mounted on a stage 32, and a laser beam is irradiated to the wafer 31 while moving the stage 32. In other words, when a measurement is conducted by using the foreign substance inspection apparatus comprising a laser irradiation instrument 29 and scattered light detectors 30, 30', if a foreign substance is present in the photoresist film on the wafer 31, the laser beam is scattered by this foreign substance. In this way, the foreign substance in the wafer is detected and located by the scattered light detectors 30, 30' ("Rinsing method for locating stain in a semiconductor wafer", Yoshiichi Konishi, 1988).

However, the above-mentioned conventional method of inspecting foreign substances could not locate foreign substances in the form of, for example, gels which were created inside a photoresist film. This problem will be explained by using FIGS. 6(a) and 6(b). FIGS. 6(a) and 6(b) are partial cross-sectional views of a wafer showing a problem which is intended to be solved by this invention. With the above-mentioned conventional apparatus of inspecting foreign substances in a photoresist film, it was extremely difficult to detect, for example, a gel foreign substance 33 shown in FIG. 6(a) which was present inside a photoresist film 34. Furthermore, as shown in FIG. 6(b), when a gel foreign substance is present between patterns after the photoresist was developed, it is also difficult to detect the foreign substance because of a photoresist pattern 35 in the vicinity which reflects the light irregularly. In particular, when the gel foreign substance 33 is present between the patterns 35 as shown in FIG. 6(b), it causes a pattern failure.

SUMMARY OF THE INVENTION

It is an object of this invention to solve the above-mentioned problems in conventional systems by providing a method and an apparatus for inspecting for foreign substances in a photoresist film, to ensure detection of gel foreign substances which are present inside a photoresist film or between resist patterns.

In order to accomplish these and other objects and advantages, a method of inspecting foreign substances on a substrate surface of this invention comprises the steps of applying a photoresist on the surface of a substrate, exposing the photoresist, removing the exposed photoresist using a developing solution, irradiating a laser beam on the substrate surface which has the photoresist removed, and intercepting the scattered light to detect whether a foreign substances is present or not. According to this configuration, the photoresist is exposed, developed, and removed, so if a gel foreign substance is present inside a photoresist film or between patterns, this foreign substance is exposed. Therefore, it is possible to surely detect the presence of a foreign substance with a foreign substance inspection apparatus which has been used conventionally.

Next, an apparatus for inspecting for foreign substances on a substrate surface of this invention comprises a means for applying a photoresist on the surface of a substrate, a means for exposing the photoresist, a means for removing the exposed photoresist using a developing solution, and a means of irradiating a laser beam on the substrate surface which has the photoresist removed and detecting foreign substances by intercepting the scattered light. Accordingly, gel foreign substances which are present inside a resist film or between resist patterns can be detected surely and efficiently.

It is preferable in the above-mentioned method and apparatus of this invention that after the photoresist is removed with an alkali developing solution, ultraviolet rays are irradiated in an inactive atmosphere while heating at a temperature of from 150 to 250° C. Thus, it is possible to generate a cross-linking reaction in a gel foreign substance and to prevent the gel foreign substance from changing its shape, so that the presence of a foreign substance can be detected surely even if an inspection takes place a long time after the photoresist was removed. In t his instance, the inactive atmosphere comprises, for example, an atmosphere of gaseous nitrogen.

Furthermore, it is preferable in this invention that the heating means comprises a hot plate, since a hot plate has excellent heating efficiency.

Also, it is preferable in this invention that after the photoresist is removed with an alkali developing solution, the substrate surface is subjected to an etching process and an ashing process, which is followed by washing the substrate. By exposing the photoresist and conducting the etching process using a gel foreign substance which remained through the development as a mask, gel foreign substances which are present in the photoresist film or between patterns can be detected.

In addition, it is preferable in this invention that the etching process comprises a method of etching a substrate surface with an average depth of 0.1 to 1 $\mu$m using a reactive ion etching means. When it is etched with an average depth of 0.1 to 1 $\mu$m, foreign substances can be detected accurately by irradiating a laser beam and intercepting its scattered light.

It is preferable in this invention that the ashing process comprises a method of heating a substrate surface at an average temperature of 200 to 300° C. using a reactive ion etching means. Under this condition, gel foreign substances which remain between resist patterns can be ashed surely.

Furthermore, it is preferable in this invention that the method of applying a photoresist on a substrate comprises a rotary-coating (spin-coating) method. This is because this method enables a thin and an uniform coating of a photoresist. Furthermore, examples of photoresist include a resin which blocked a hydroxyl group of poly(p-vinylphenol) with t-butylester, a composition comprising a soluble polymer such as polyvinylalcohol (PVA) mixed with a photocrosslinking agent such as ammonium dichromate, a multifunctional diazonium salt, a soluble bisazide compound, or a compound comprising a subring polyisoprene mixed with a bisazide compound (for example, 2,6-(4-azidebenzal) methycyclohexane), naphthoquinone diazide, and a novolak resin.

In addition, it is preferable in the above-mentioned invention that the method of removing a photoresist using a developing solution is performed by using at least one solution selected from the group comprising an inorganic alkali aqueous solution and tetramethyl ammonium hydroxide. These solutions are suitable for dissolving a resist.

Also, it is preferable that the method of washing a substrate after an ashing process is performed by using an aqueous solution containing sulfuric acid and hydrogen peroxide. The use of this aqueous solution enables surely removing ashed gel foreign substances.

It is preferable in this invention that the substrate comprises at least one substrate selected from the group comprising a semiconductor substrate, a printed circuit substrate, a connector substrate for electric connection, a nesa glass for liquid crystal display element, and various sensor substrates. These substrates can be suitably used as a substrate which is required to be patterned accurately and minutely using a resist.

According to the above-described method of this invention, the photoresist is exposed, developed, and then removed. As a result, if a gel foreign substance is present inside a photoresist film or between patterns, this foreign substance is exposed, so that its presence can be detected surely with an inspection apparatus of foreign substances which has been used conventionally.

Also, according to the apparatus of this invention, gel foreign substances which are present in a resist film or between resist patterns can be detected surely and efficiently.

According to the above-mentioned preferable method of inspecting foreign substances on a substrate surface of this invention, the method comprises the steps of applying a photoresist on the surface of a substrate, exposing the photoresist, removing the exposed photoresist using a developing solution, performing an etching process and an ashing process on the substrate surface, washing the substrate, irradiating a laser beam on the substrate surface after some time, and detecting foreign substances by intercepting the scattered light. In this way, gel foreign substances which are present inside a resist film or between resist patterns can be detected surely. In other words, by exposing the photoresist and conducting the etching process using a gel foreign substance which remained through the development as a mask, gel foreign substances which are present in the photoresist film or between patterns can be detected.

Next, according to the apparatus of inspecting foreign substances on a substrate surface of this invention, the apparatus comprises a means for applying a photoresist on the surface of a substrate, a means for exposing the photoresist, a means for removing the exposed photoresist using a developing solution, a means of etching and ashing the substrate surface, a means of washing the substrate, and a means of irradiating a semiconductor laser beam on the substrate surface and intercepting the scattered light for detecting foreign substances. In this way, gel foreign substances which are present inside a resist film or between resist patterns can be detected surely and efficiently.

This invention can be applied to various usages using a resist, for example, a semiconductor substrate, a printed circuit substrate, a connector substrate for electric connection, a nesa glass for liquid crystal display element, and various sensor substrates.

BRIEF DESCRIPTION OF THE DRAWINGS

FIGS. 1(a) to 1(f) are cross-sectional views showing a method of manufacturing a wafer for inspecting a gel foreign substance in a photoresist film in one embodiment of this invention. FIG. 1(a) shows a step of rotary-coating (spin-coating) a photoresist on a wafer; FIG. 1(b) shows a step of irradiating ultraviolet rays to the coated photoresist and exposing the photoresist; FIG. 1(c) shows a step of removing the exposed photoresist with an alkali developing solution; FIG. 1(d) shows a step of etching the wafer which has the photoresist removed; FIG. 1(e) shows a step of ashing and washing the etched wafer; and FIG. 1(f) shows a step of irradiating a semiconductor laser beam to the wafer surface and detecting foreign substances from reflected scattered light.

FIGS. 3(a) to 3(e) are schematic cross-sectional views showing a method of inspecting foreign substances in this invention. FIG. 3(a) shows a step of rotary-coating a photoresist on a semiconductor substrate; FIG. 3(b) shows a step of irradiating ultraviolet rays to the applied photoresist using an exposure instrument such as a stepper and entirely exposing the photoresist on the semiconductor substrate; FIG. 3(c) shows a step of removing the exposed photoresist with an alkali developing solution; FIG. 3(d) shows a step of irradiating a laser beam to the semiconductor substrate which has the photoresist removed and inspecting the presence of foreign substances from light scattering at the surface; FIG. 3(e) shows a step of irradiating with ultraviolet rays while heating the semiconductor substrate at a temperature of 150 to 250° C. with a hot plate in an inactive atmosphere, which is conducted between Step (c) and Step (d).

DETAILED DESCRIPTION OF THE INVENTION

Figure 2:
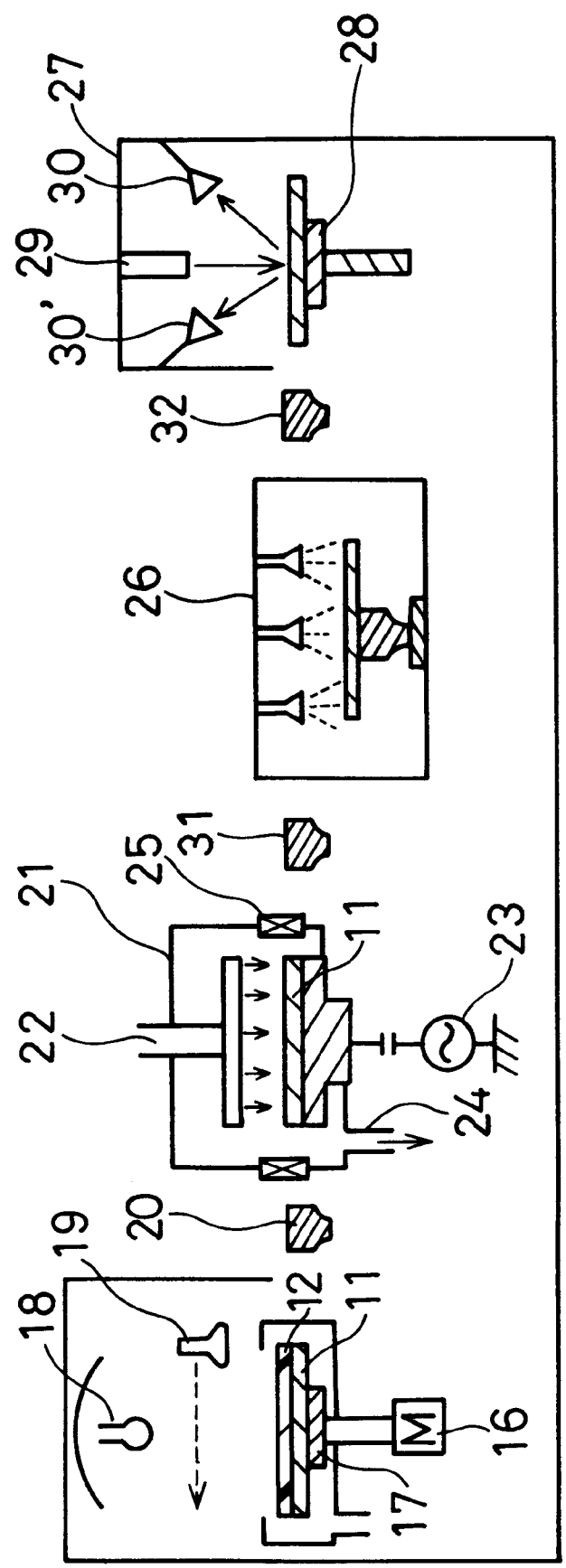
FIG. 2 is a schematic diagram showing an inspection apparatus of a wafer which is used for inspecting foreign substances inside a photoresist in one embodiment of this invention.
Figure 3A:
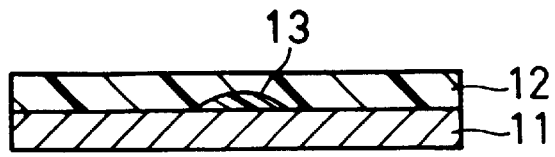
Figure 3B:
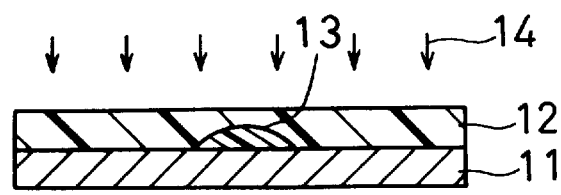
Figure 3C:
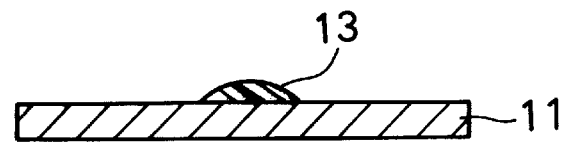
Figure 3E:
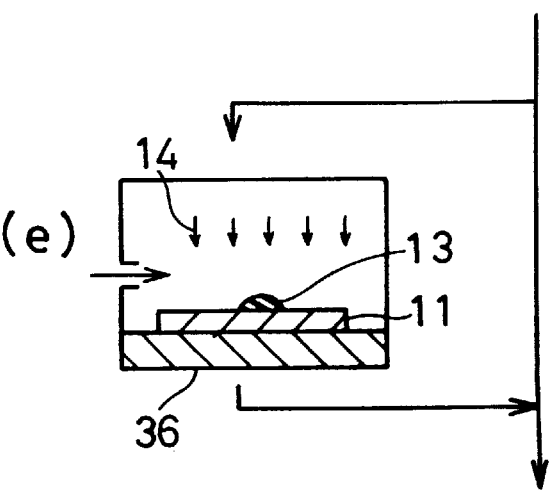

This invention will now be described in detail by referring to the attached figures and the following examples. The examples are illustrative and should not be construed as limiting the invention in any way. In the following examples, a silicon semiconductor was used as a substrate.

EXAMPLE 1

A method of manufacturing a wafer used for inspection of foreign substances in a photoresist film of this invention comprises the steps of rotary-coating a photoresist on the surface of a wafer, exposing the photoresist by irradiating ultraviolet rays (for example, exposing by using a stepper), removing the exposed photoresist with an alkali developing solution, etching, ashing, and washing the surface of the semiconductor substrate which has the photoresist removed, and irradiating a laser beam on the surface of the washed semiconductor substrate and inspecting foreign substances from the reflected scattered light. Furthermore, an apparatus for inspecting foreign substances in a photoresist film of this invention comprises a stage which is mounted with a semiconductor substrate applied with the photoresist on the entire surface, a light source part for exposing the photoresist, a part for developing the exposed photoresist, a part which etches and ashes the semiconductor substrate which has the photoresist removed, a part which washes the ashed semiconductor substrate, and a light-intercepting part which irradiates a semiconductor laser on the surface of the semiconductor substrate and catches the scattered light.

FIGS. 1(a) to 1(f) show steps of manufacturing a wafer used for inspection of gel foreign substances in a photoresist in one embodiment of this invention. As shown in FIG. 1(a), first, a photoresist 12 is rotary-coated (spin-coated) on the surface of a silicon semiconductor wafer 11 having a diameter of 6 inches and a thickness of 0.6 mm. The wafer 11 comprises a silicon semiconductor or a compound semiconductor such as Ga-As. Examples of the photoresist 12 include a resin which blocked a hydroxyl group of poly(p-vinylphenol) with t-butylester, a composition comprising a soluble polymer such as polyvinylalcohol (PVA) mixed with a photo-crosslinking agent such as ammonium dichromate, a multifunctional diazonium salt, a soluble bisazide compound, or a compound comprising a subring polyisoprene mixed with a bisazide compound (for example, 2,6-(4-azidebenzal)methycyclohexane), naphthoquinone diazide, and a novolak resin. In this embodiment, a resin which blocked a hydroxyl group of poly(p-vinylphenol) with t-butylester was used.

The photoresist 12 is preferably coated at a thickness of about 1.0 $\mu$m after being dried. During this process, a gel foreign substance 13 is created at a boundary face of the wafer 11 and the photoresist 12 or inside the photoresist film 12.

Next, as shown in FIG. 1(b), ultraviolet rays 14 are irradiated onto the coated photoresist 12 using an exposure instrument such as a stepper, and the entire wafer 11 is exposed. It is preferable to irradiate the ultraviolet rays 14 for about 30 seconds and at an amount of about 500 mJ.

Then, as shown in FIG. 1(c), the exposed photoresist 12 is removed with an alkali developing solution. The alkali developing solution used here is, for example, tetramethyl ammonium hydroxide. The photoresist 12 is dipped in the aqueous solution with the concentration of 2.38 weight percent for about 60 seconds.

Subsequently, as shown in FIG. 1(d), the wafer 11 which has the photoresist 12 removed is etched using, for example, a RIE (reactive ion etching apparatus) etcher. The etching conditions are $SF_6/O_2$=50/10 sscm, pressure: 10 to 30 Pa, temperature: 100 to 120° C., high frequency electric power: RF=200 to 300 W. According to this etching treatment, the wafer 11 was etched into a depth of about 0.5 $\mu$m from the surface.

Then, as shown in FIG. 1(e), the etched wafer 11 is ashed and washed. The ashing process comprises, for example, an $O_2$ plasma ashing under the conditions of pressure: 40 to 50 Pa, wafer temperature: 50 to 200° C., and high frequency electric power: RF=1 KW. According to this ashing treatment, the surface of the wafer 11 was ashed to a gel foreign substance 13. Subsequently, the wafer 11 was washed with an aqueous solution of sulfuric acid/hydrogen peroxide and then with pure water, and the ashed substance was removed.

After these processes of ashing and washing are over, the wafer 11 was dried. Then, a semiconductor laser beam was irradiated on the surface of the wafer 11 to inspect foreign substances from reflected scattered light (FIG. 1(f)). The semiconductor laser beam comprises, for example, a semiconductor laser beam of He—Ne, and it is preferable that the laser beam has a wavelength of from 600 to 700 nm. The amount of irradiation is from 1 to 10 mW.

The foreign substance 13 inside the photoresist film is usually considered to be a gel foreign substance. Since the foreign substance does not dissolve even after the exposure treatment and the development treatment were conducted to the photoresist, this gel foreign substance 13 serves as a mask during the etching process, as shown in FIG. 1(d). In this way, the semiconductor substrate is etched except for the part below the gel foreign substance 13. Subsequently, after the gel foreign substrate 13 is removed through ashing and washing, a protrusion 15 is formed on the semiconductor substrate. This protrusion 15 can be detected easily as a foreign substance with a foreign substance inspection apparatus in a short time.

EXAMPLE 2

FIG. 2 shows an apparatus for manufacturing and inspecting a wafer used for inspection of foreign substances inside a photoresist in one embodiment of this invention. As for a foreign substance inspection apparatus 27, a conventional apparatus can be used. As shown in FIG. 2, before arriving at the foreign substance inspection apparatus 27, there are a stage 17 provided with a spin motor 16, a mercury lamp 18 which exposes a photoresist 12 of a wafer 11 mounted on this stage 17, a nozzle 19 for dripping a developing solution for developing the exposed photoresist 11, a transfer instrument 20 for forwarding the wafer, an etching unit 21 for etching and ashing the substrate, and a cleaning unit 26.

A RIE (reactive ion etching apparatus) etcher can be used as the above-mentioned etching unit 21 mainly comprising a high frequency generator 23, an air outlet 24 connected to a turbo pump (not shown in the figure), and a valve 25. Gas (HBr-type) is let in from a gas inlet 22, and the (Si) surface of the wafer 11 is etched. Furthermore, the cleaning unit 26 comprises an aqueous solution of sulfuric acid/hydrogen peroxide.

The above-mentioned foreign substance inspection apparatus 27 is comprised of a stage 28 which is mounted with the wafer 11, a laser beam irradiation instrument 29, and scattered light detectors 30, 30'. In this figure, 31 and 32 are transfer instruments for forwarding the wafer.

Next, the operation of the above-configured foreign apparatus of inspecting foreign substance in a photoresist film will be explained. First, the wafer 11 which is rotary-coated with the photoresist 12 is mounted on the stage 17. Next, the mercury lamp 18 is irradiated on the surface of the photoresist, and the developing solution is dripped while moving the nozzle 19. A gel foreign substance which is present inside the film of the photoresist 12 is not developed and remains on the wafer. Then, the wafer with the gel foreign substance remaining on the surface is transferred to the etching unit 21, where etching and ashing treatments take place using plasma.

This etching is conducted to etch the semiconductor substrate to a depth of about 0.5 µm. At this time, the gel foreign substance serves as a mask, so that the semiconductor substrate remains in the form of protrusion. Thereafter, the wafer is transferred to the cleaning unit 26, where it is washed in an aqueous solution of sulfuric acid/hydrogen peroxide and foreign substances adhered on the semiconductor surface are washed off with the RIE dry etcher. Then, this protrusion disposed on the semiconductor substrate is detected as a foreign substance by the above-mentioned foreign substance inspection apparatus 27.

It was confirmed that the application of this method of manufacturing a wafer for inspection of foreign substances inside a photoresist film and the application of a manufacturing and inspection apparatus enabled detection of gel foreign substances, which were difficult to be detected using a conventional inspection apparatus. In addition, this invention can also detect foreign substaces in a short time, whereas the detection using a pattern failure inspection apparatus takes a long time.

As explained above, the embodiment of this invention can surely detect gel foreign substaces which are present inside a photoresist film or between patterns by exposing a photoresist, performing an etching process using a gel foreign substance which remained through a development as a mask, and ashing.

EXAMPLE 3

FIGS. 3(a) to 3(d) show steps of inspecting gel foreign substances contained in a photoresist film in another embodiment of this invention. The same explanation as that of Example 1 is omitted. First, this method comprises a step of rotary-coating a photoresist 12 on the surface of a semiconductor substrate 11 (FIG. 3(a)), a second step of irradiating ultraviolet rays 14 on the coated photoresist 12 using an exposure apparatus such as a stepper and exposing the entire photoresist 12 disposed on the semiconductor substrate 11(FIG. 3( b)), a third step of removing the exposed photoresist 12 with an alkali developing solution (FIG. 3(c)), and a fourth step of irradiating a laser beam onto the semiconductor substrate 11 which has the photoresist 12 removed and inspecting the presence of a foreign substance from the scattered light at the surface (FIG. 3(d)).

The foreign substance contained in the photoresist 12 is usually considered as a gel foreign substance. This substance does not dissolve even after the processes of exposure or development. By using this property, the gel foreign substance can be left on the semiconductor substrate 11 by the exposure and the development of the photoresist 12. In other words, in the method of this embodiment, the photoresist 12 is exposed, developed and then removed, so if a gel foreign substance is present inside the photoresist 12 or between the patterns, this substance is exposed by the removal of the photoresist 12. Thus, a conventional foreign substance inspection apparatus can surely detect whether a gel foreign substance is present or not.

EXAMPLE 4

By the way, when a gel foreign substance resulting from a photoresist is left, its shape changes such that it becomes difficult to detect, that is, the substrate becomes lower. This is considered to result from the fact that moisture evaporates which is contained inside the gel foreign substance in a large amount.

As a method of solving the difficulty in the detection arising from this kind of shape change in the gel foreign substance, a fifth step is provided between the third step and the fourth step mentioned in Example 3, in which the semiconductor substrate 11 is placed on a hot plate 15 and the ultraviolet rays 14 are irradiated while heating the semiconductor substrate 11 with the hot plate 14 in an inactive atmosphere of nitrogen ($N_2$) and the like at a temperature of from 150 to 250° C. (FIG. 3(e)).

This fifth step allows a polymerization reaction to take place in the gel foreign substance and prevents the shape from changing. As a result, the inconvenience or the difficulty related to the detection of foreign substances which were left for a long time until an inspection takes place after the photoresist 12 was removed can be solved with this step.

Figure 4:
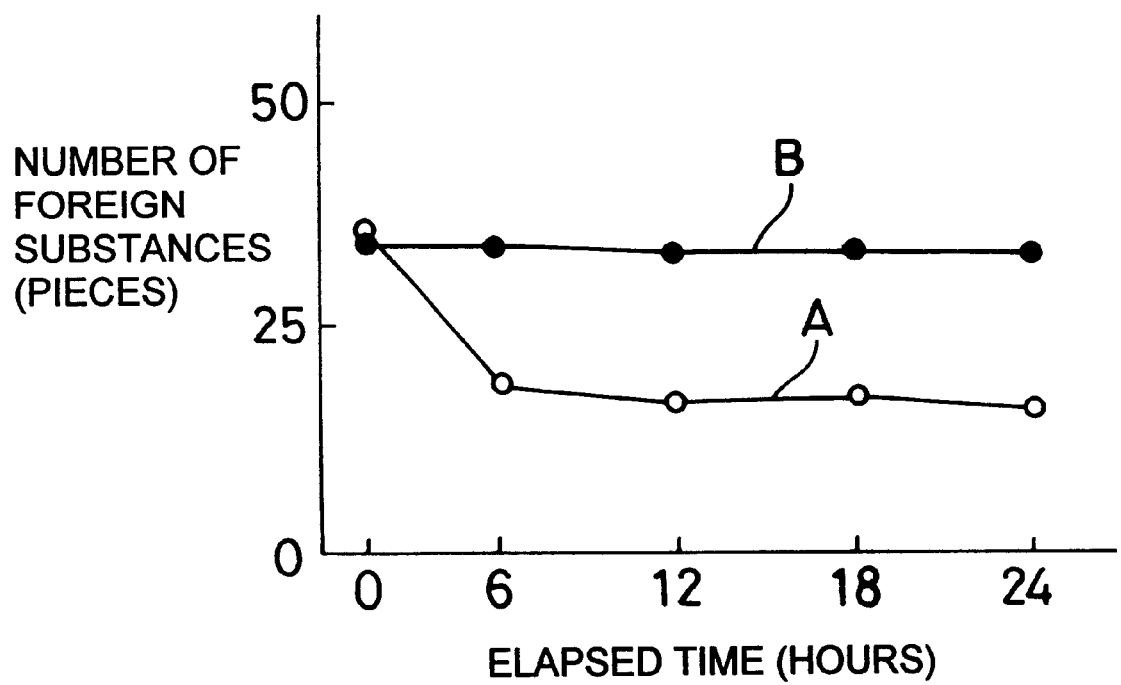
FIG. 4 is a graph showing a changing number of gel foreign substances over time which are detected by methods described in Example 3 and Example 4 of this invention.
Figure 5:
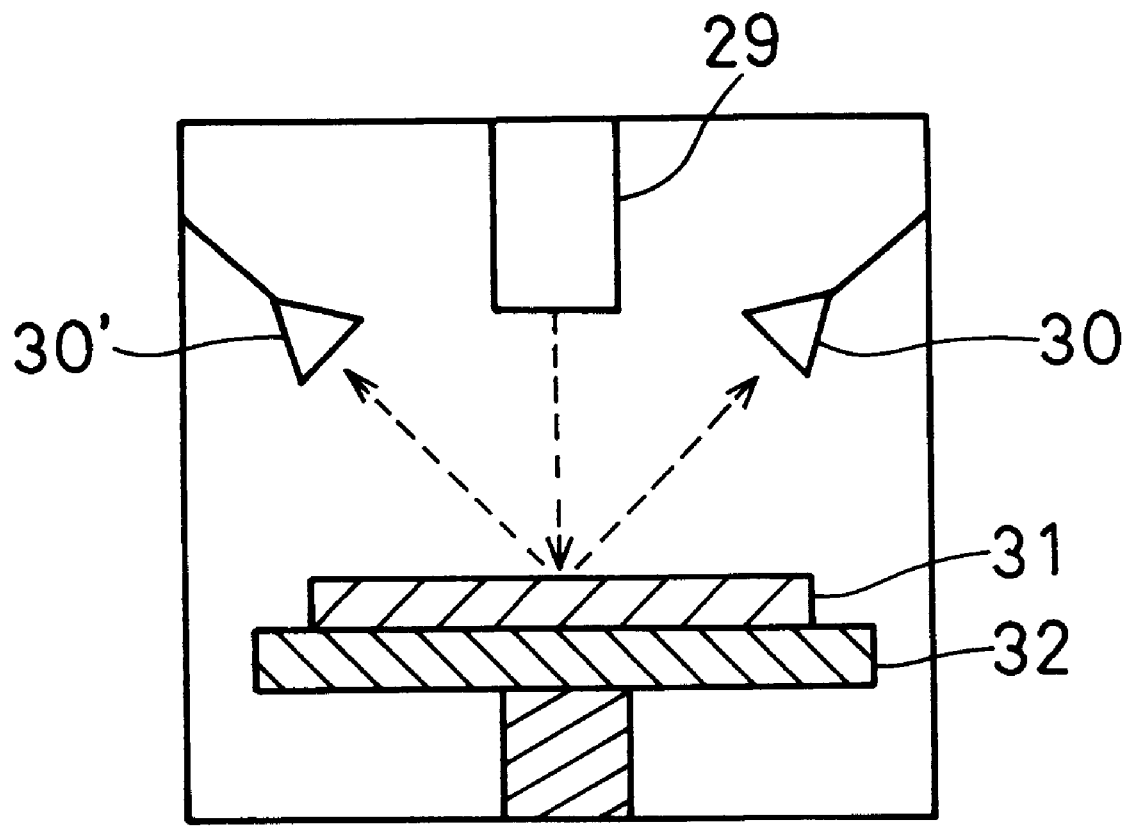
FIG. 5 is a schematic diagram showing a structure in one embodiment of a conventional foreign substance inspection apparatus.
Figure 6:
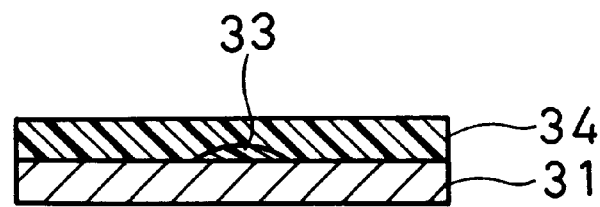
FIGS. 6(a) and 6(b) are partial cross-sectional views showing a wafer which was inspected with a conventional foreign substance inspection apparatus.
Figure 6:
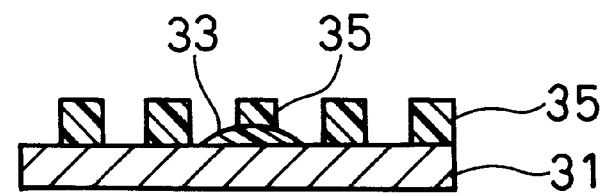

FIG. 4 shows numbers of gel foreign substances detected with the methods of Example 3 and Example 4 along with the elasped time from the manufacture of the semiconductor substrate for inspection of gel foreign substances to the inspection of foreign substances. In FIG. 4, A indicates a changing number of gel foreign substances detected by the method of Example 3, and B indicates a changing number of gel foreign substances detected by the method of Example 4. As clearly shown in this graph, it is preferable in Example 3 to inspect the presence of foreign substances shortly after the semiconductor substrate for detection of gel foreign substances is manufactured. On the other hand, according to Example 4, even if a long time elapsed from the manufacture of the semiconductor substrate for inspection of gel foreign substances until the inspection of foreign substances, it is possible to easily detect whether gel foreign substances are present or not.

By applying the above-mentioned method of inspecting foreign substances, the presence of foreign substances can be confirmed in a short time, whereas it took a long time in the past. This method is useful for the manufacturing line.

According to this embodiment, the photoresist is exposed, developed, and removed, so that gel foreign substances which are present in the photoresist or between the patterns can be detected surely.

The invention may be embodied in other forms without departing from the spirit or essential characteristics thereof. The embodiments disclosed in this application are to be considered in all respects as illustrative and not as restrictive. The scope of the invention is indicated by the appended claims rather than by the foregoing description, and all changes which come within the meaning and range of equivalency of the claims are intended to be embraced therein.

What is claimed is:

1. A method for detecting gel substances formed in a photoresist on a substrate surface, comprising:

applying a positive photoresist on the surface of a substrate;

exposing the entire surface to which the photoresist was applied;

removing the exposed photoresist;

irradiating the substrate surface from which the photoresist has been removed with ultraviolet rays in an inactive atmosphere while heating the substrate surface at a temperature of from 150 to 250° C. to allow a polymerization reaction to take place in any gel substances on the substrate surface;

irradiating a laser beam on the substrate surface after the irradiation with ultraviolet rays and heating step; and intercepting light from the laser beam to detect whether a gel substance is present or not due to scattering of light by the gel substance.

2. The method of claim 1, wherein the heating is conducted with a hot plate.

3. The method of claim 1, wherein the photoresist is applied to the substrate by spin-coating.

4. The method of claim 1, wherein the photoresist is removed using a developing solution.

5. The method of claim 4, wherein the developing solution is selected from the group consisting of an inorganic alkali aqueous solution and tetramethyl ammonium hydroxide.

6. The method of claim 1, wherein the substrate is selected from the group consisting of a semiconductor substrate, a printed circuit substrate, a connector substrate for electric connection, a nesa glass from a liquid crystal display element and a sensor substrate.

7. A method of inspecting for gel substances formed in a photoresist on a substrate surface, comprising the steps of:

applying a positive photoresist to the surface of a substrate;

exposing the entire surface to which the photoresist was applied;

removing the exposed photoresist;

subjecting the exposed surface to etching, whereby any gel substances on the substrate act as a mask for the etching;

irradiating a laser beam on the substrate surface after etching; and intercepting light from the laser beam to detect whether a gel substance was present or not during the etching step due to scattering of light by protrusions generated by the etching step in which gel substances on the substrate act as a mask for the etching.

8. The method of claim 7, wherein, between the etching and irradiating steps, the substrate surface is subjected to ashing, followed by washing.

9. The method of claim 8, wherein the ashing process comprises a method of heating the substrate surface at an average temperature of 200 to 300° C. using a reactive ion etching apparatus.

10. The method claim 8, wherein the step of washing after ashing is performed with an aqueous solution comprising sulfuric acid and hydrogen peroxide.

11. The method of claim 7, wherein the etching step etches the substrate surface to an average depth of 0.1 to 1 $\mu$m.

12. The method of claim 11, wherein the etching is carried out using a reactive ion etching apparatus.

13. The method of claim 7, wherein the photoresist is applied to the substrate by spin-coating.

14. The method of claim 7, wherein the photoresist that is removed from the substrate surface with a developing solution.

15. The method of claim 14, wherein the developing solution is selected from the group consisting of an inorganic alkali aqueous solution and tetramethyl ammonium hydroxide.

16. The method of claim 7, wherein the substrate is selected from the group consisting of a semiconductor substrate, a printed circuit substrate, a connector substrate for electric connection, a nesa glass for a liquid crystal display element and a sensor substrate.

* * * * *